US007635389B2

(12) United States Patent
Yu et al.

(10) Patent No.: US 7,635,389 B2
(45) Date of Patent: Dec. 22, 2009

(54) POSTERIOR JOINT REPLACEMENT DEVICE

(75) Inventors: Kidong Yu, Memphis, TN (US);
Richard G. Fessler, Winnetka, IL (US)

(73) Assignee: Warsaw Orthopedic, Inc.

( * ) Notice: Subject to any disclaimer, the term of this patent is extended or adjusted under 35 U.S.C. 154(b) by 107 days.

(21) Appl. No.: 11/342,961

(22) Filed: Jan. 30, 2006

(65) Prior Publication Data

US 2007/0191945 A1   Aug. 16, 2007

(51) Int. Cl.
*A61F 2/44* (2006.01)
(52) U.S. Cl. .................. 623/17.15; 623/17.14
(58) Field of Classification Search .................. 606/61, 606/246–279; 623/17.11–17.16
See application file for complete search history.

(56) References Cited

U.S. PATENT DOCUMENTS

| | | |
|---|---|---|
| 4,349,921 A | 9/1982 | Kuntz |
| 4,697,582 A | 10/1987 | Williams |
| 4,697,586 A | 10/1987 | Gazale |
| 4,702,930 A | 10/1987 | Heide et al. |
| 4,759,769 A | 7/1988 | Hedman et al. |
| 4,836,196 A | 6/1989 | Park et al. |
| 4,932,975 A | 6/1990 | Main et al. |
| 5,092,866 A | 3/1992 | Breard et al. |
| 5,258,031 A | 11/1993 | Salib et al. |
| 5,282,863 A | 2/1994 | Burton |
| 5,387,213 A | 2/1995 | Breard et al. |
| 5,401,269 A | 3/1995 | Buttner-Janz et al. |
| 5,415,661 A | 5/1995 | Holmes |
| 5,423,825 A | 6/1995 | Levine |
| 5,443,515 A | 8/1995 | Cohen et al. |
| 5,458,864 A | 10/1995 | Tsugeno et al. |
| 5,507,816 A | 4/1996 | Bullivant |

(Continued)

FOREIGN PATENT DOCUMENTS

DE  101 35771 A1  2/2003

(Continued)

OTHER PUBLICATIONS

Patent Cooperation Treaty—European Patent Office, "Notification of Transmittal of the International Search Report and The Written Opinion of the International Searching Authority, or the Declaration," International Application No. PCT/US2007/060491, Apr. 25, 2007, 12 pages.

(Continued)

*Primary Examiner*—Thomas C Barrett
*Assistant Examiner*—Andrew Yang

(57) ABSTRACT

A prosthetic device for placement in an intervertebral space defined between an upper vertebra and a lower vertebra to provide articulating motion to the upper and lower vertebrae may includes an upper articular portion configured to be at least partially disposed in the intervertebral space and a lower articular portion configured to be at least partially disposed in the intervertebral space. The lower articular portion may be configured to cooperate with the upper articular portion to provide articulating motion to the upper and lower vertebrae. An attachment element may extend in the general direction of the spinal column. The attachment element may be configured to be fastened to at least one of the upper and the lower vertebrae to at least partially secure in place said one of the upper and lower articular portions. A method of implanting also is disclosed.

13 Claims, 6 Drawing Sheets

U.S. PATENT DOCUMENTS

| | | |
|---|---|---|
| 5,556,431 A | 9/1996 | Buttner-Janz |
| 5,562,660 A | 10/1996 | Grob |
| 5,562,737 A | 10/1996 | Graf |
| 5,562,738 A | 10/1996 | Boyd et al. |
| 5,571,109 A | 11/1996 | Bertagnoli et al. |
| 5,607,425 A | 3/1997 | Rogozinski |
| 5,672,175 A | 9/1997 | Martin |
| 5,674,296 A | 10/1997 | Bryan et al. |
| 5,676,701 A | 10/1997 | Yuan et al. |
| 5,702,450 A | 12/1997 | Bisserie |
| 5,728,098 A | 3/1998 | Sherman et al. |
| 5,752,957 A | 5/1998 | Ralph et al. |
| 5,772,661 A | 6/1998 | Michelson |
| 5,895,428 A | 4/1999 | Berry |
| 5,899,941 A | 5/1999 | Nishijima et al. |
| RE36,221 E | 6/1999 | Breard et al. |
| 5,928,284 A | 7/1999 | Mehdizadeh |
| 5,961,516 A | 10/1999 | Graf |
| 6,019,792 A | 2/2000 | Cauthen |
| 6,036,088 A | 3/2000 | Itoh et al. |
| 6,039,763 A | 3/2000 | Shelokov |
| 6,042,582 A | 3/2000 | Ray |
| RE36,758 E | 6/2000 | Fitz |
| 6,106,557 A | 8/2000 | Robioneck et al. |
| 6,113,637 A | 9/2000 | Gill et al. |
| 6,132,464 A | 10/2000 | Martin |
| 6,146,421 A | 11/2000 | Gordon et al. |
| 6,156,067 A | 12/2000 | Bryan et al. |
| 6,159,211 A | 12/2000 | Boriani et al. |
| 6,159,214 A | 12/2000 | Michelson |
| 6,159,244 A | 12/2000 | Suddaby |
| 6,174,311 B1 | 1/2001 | Branch et al. |
| 6,179,874 B1 | 1/2001 | Cauthen |
| 6,179,875 B1 | 1/2001 | Strempel |
| 6,190,414 B1 | 2/2001 | Young et al. |
| 6,193,757 B1 | 2/2001 | Foley et al. |
| 6,200,322 B1 | 3/2001 | Branch et al. |
| 6,224,599 B1 | 5/2001 | Baynham et al. |
| 6,224,607 B1 | 5/2001 | Michelson |
| 6,228,118 B1 | 5/2001 | Gordon |
| 6,231,609 B1 | 5/2001 | Mehdizadeh |
| 6,235,059 B1 | 5/2001 | Benezech et al. |
| 6,251,112 B1 | 6/2001 | Jackson |
| 6,277,122 B1 | 8/2001 | McGahan et al. |
| 6,325,827 B1 | 12/2001 | Lin |
| 6,368,350 B1 | 4/2002 | Erickson et al. |
| 6,402,750 B1 | 6/2002 | Atkinson et al. |
| 6,409,766 B1 | 6/2002 | Brett |
| 6,419,703 B1 | 7/2002 | Fallin et al. |
| 6,419,705 B1 | 7/2002 | Erickson |
| 6,432,140 B1 | 8/2002 | Lin |
| 6,440,139 B2 | 8/2002 | Michelson |
| 6,440,168 B1 | 8/2002 | Cauthen |
| 6,454,807 B1 | 9/2002 | Jackson |
| 6,471,724 B2 | 10/2002 | Zdeblick et al. |
| 6,514,260 B1 | 2/2003 | Zdeblick et al. |
| 6,517,580 B1 | 2/2003 | Ramadan et al. |
| 6,524,312 B2 | 2/2003 | Landry et al. |
| 6,527,804 B1 | 3/2003 | Gauchet et al. |
| 6,540,747 B1 | 4/2003 | Marino |
| 6,540,785 B1 | 4/2003 | Gill et al. |
| 6,562,074 B2 | 5/2003 | Gerbec et al. |
| 6,565,571 B1 | 5/2003 | Jackowshi et al. |
| 6,565,574 B2 | 5/2003 | Michelson |
| 6,565,605 B2 | 5/2003 | Goble et al. |
| 6,572,653 B1 | 6/2003 | Simonson |
| 6,579,319 B2 | 6/2003 | Goble et al. |
| 6,582,466 B1 | 6/2003 | Gauchet |
| 6,582,468 B1 | 6/2003 | Gauchet |
| 6,589,247 B2 | 7/2003 | McGahan et al. |
| 6,599,291 B1 | 7/2003 | Foley et al. |
| 6,610,065 B1 | 8/2003 | Branch et al. |
| 6,610,091 B1 | 8/2003 | Reiley |
| 6,610,093 B1 | 8/2003 | Pisharodi |
| 6,641,582 B1 | 11/2003 | Hanson et al. |
| 6,641,614 B1 | 11/2003 | Wagner et al. |
| 6,648,895 B2 | 11/2003 | Burkus et al. |
| 6,669,729 B2 | 12/2003 | Chin |
| 6,679,915 B1 | 1/2004 | Cauthen |
| 6,685,742 B1 | 2/2004 | Jackson |
| 6,692,495 B1 | 2/2004 | Zacouto |
| 6,699,247 B2 | 3/2004 | Zucherman et al. |
| 6,709,458 B2 | 3/2004 | Michelson |
| 6,733,532 B1 | 5/2004 | Gauchet et al. |
| 6,743,255 B2 | 6/2004 | Ferree |
| 6,749,635 B1 | 6/2004 | Bryan |
| 6,805,714 B2 | 10/2004 | Sutcliffe |
| 6,811,567 B2 | 11/2004 | Reiley |
| 6,908,484 B2 | 6/2005 | Zubok et al. |
| 6,949,123 B2 | 9/2005 | Reiley |
| 6,984,245 B2 | 1/2006 | McGahan et al. |
| 6,986,772 B2 | 1/2006 | Michelson |
| 6,994,727 B2 | 2/2006 | Khandkar et al. |
| 7,025,787 B2 | 4/2006 | Bryan et al. |
| 7,044,971 B2 | 5/2006 | Suddaby |
| 7,052,515 B2 | 5/2006 | Simonson |
| 7,070,598 B2 | 7/2006 | Lim et al. |
| 7,074,240 B2 | 7/2006 | Pisharodi |
| 7,083,649 B2 | 8/2006 | Zucherman et al. |
| 7,083,650 B2 | 8/2006 | Moskowitz et al. |
| 7,090,698 B2 | 8/2006 | Goble et al. |
| 7,137,985 B2 * | 11/2006 | Jahng .................... 606/61 |
| 7,147,665 B1 | 12/2006 | Bryan et al. |
| 7,282,065 B2 | 10/2007 | Kirschman |
| 7,291,150 B2 | 11/2007 | Graf |
| 7,311,732 B2 | 12/2007 | Link et al. |
| 7,338,525 B2 | 3/2008 | Ferree |
| 7,338,527 B2 | 3/2008 | Blatt et al. |
| 2001/0005796 A1 | 6/2001 | Zdeblick et al. |
| 2001/0010021 A1 | 7/2001 | Boyd et al. |
| 2001/0016773 A1 | 8/2001 | Serhan et al. |
| 2001/0016774 A1 | 8/2001 | Bresina et al. |
| 2001/0032020 A1 | 10/2001 | Besselink |
| 2001/0034553 A1 | 10/2001 | Michelson |
| 2001/0047207 A1 | 11/2001 | Michelson |
| 2001/0049560 A1 | 12/2001 | Paul et al. |
| 2002/0045943 A1 | 4/2002 | Uk |
| 2002/0049394 A1 | 4/2002 | Roy et al. |
| 2002/0049497 A1 | 4/2002 | Mason |
| 2002/0052656 A1 | 5/2002 | Michelson |
| 2002/0068976 A1 | 6/2002 | Jackson |
| 2002/0068977 A1 | 6/2002 | Jackson |
| 2002/0077702 A1 | 6/2002 | Castro |
| 2002/0095154 A1 | 7/2002 | Atkinson et al. |
| 2002/0095155 A1 | 7/2002 | Michelson |
| 2002/0107572 A1 | 8/2002 | Foley et al. |
| 2002/0116065 A1 | 8/2002 | Jackson |
| 2002/0123806 A1 | 9/2002 | Reiley |
| 2002/0128712 A1 | 9/2002 | Michelson |
| 2002/0128713 A1 | 9/2002 | Ferree |
| 2002/0133155 A1 | 9/2002 | Ferree |
| 2002/0137146 A1 | 9/2002 | Choi et al. |
| 2002/0138143 A1 | 9/2002 | Grooms et al. |
| 2002/0143399 A1 | 10/2002 | Sutcliffe |
| 2002/0151895 A1 | 10/2002 | Soboleski et al. |
| 2002/0151976 A1 | 10/2002 | Foley et al. |
| 2002/0156528 A1 | 10/2002 | Gau |
| 2002/0161366 A1 | 10/2002 | Robie et al. |
| 2002/0169508 A1 | 11/2002 | Songer et al. |
| 2002/0183756 A1 | 12/2002 | Michelson |
| 2003/0004572 A1 | 1/2003 | Gobel et al. |
| 2003/0004575 A1 | 1/2003 | Erickson |
| 2003/0009226 A1 | 1/2003 | Graf |
| 2003/0028250 A1 | 2/2003 | Reiley et al. |

| | | |
|---|---|---|
| 2003/0040797 A1 | 2/2003 | Fallin et al. |
| 2003/0055427 A1 | 3/2003 | Graf |
| 2003/0074068 A1 | 4/2003 | Errico et al. |
| 2003/0078666 A1 | 4/2003 | Ralph et al. |
| 2003/0100949 A1 | 5/2003 | Michelson |
| 2003/0135278 A1 | 7/2003 | Eckman |
| 2003/0139812 A1 | 7/2003 | Garcia et al. |
| 2003/0139813 A1 | 7/2003 | Messerli et al. |
| 2003/0171813 A1 | 9/2003 | Kiester |
| 2003/0176923 A1 | 9/2003 | Keller et al. |
| 2003/0191532 A1 | 10/2003 | Goble et al. |
| 2003/0199981 A1 | 10/2003 | Ferree |
| 2003/0199982 A1 | 10/2003 | Bryan |
| 2003/0204259 A1 | 10/2003 | Goble et al. |
| 2003/0204260 A1 | 10/2003 | Ferree |
| 2003/0204261 A1 | 10/2003 | Eisermann et al. |
| 2003/0204271 A1 | 10/2003 | Ferree |
| 2003/0208273 A1 | 11/2003 | Eisermann et al. |
| 2003/0233146 A1 | 12/2003 | Grinberg et al. |
| 2004/0002712 A1 | 1/2004 | Grinberg et al. |
| 2004/0002761 A1 | 1/2004 | Rogers et al. |
| 2004/0002762 A1 | 1/2004 | Hawkins |
| 2004/0006391 A1 | 1/2004 | Reiley |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034430 A1 | 2/2004 | Falahee |
| 2004/0039385 A1 | 2/2004 | Mazda et al. |
| 2004/0039448 A1 | 2/2004 | Pisharodi |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049279 A1 | 3/2004 | Sevrain |
| 2004/0049281 A1 | 3/2004 | Reiley |
| 2004/0068318 A1 | 4/2004 | Coates et al. |
| 2004/0073311 A1 | 4/2004 | Ferree |
| 2004/0097931 A1* | 5/2004 | Mitchell ............... 606/61 |
| 2004/0098131 A1 | 5/2004 | Bryan et al. |
| 2004/0102848 A1 | 5/2004 | Michelson |
| 2004/0111161 A1 | 6/2004 | Trieu |
| 2004/0126407 A1 | 7/2004 | Falahee |
| 2004/0127991 A1 | 7/2004 | Ferree |
| 2004/0133281 A1 | 7/2004 | Khandkar et al. |
| 2004/0138749 A1 | 7/2004 | Zucherman et al. |
| 2004/0143270 A1 | 7/2004 | Zucherman et al. |
| 2004/0162562 A1 | 8/2004 | Martz |
| 2004/0162618 A1 | 8/2004 | Mujwid et al. |
| 2004/0176764 A1 | 9/2004 | Dant |
| 2004/0176845 A1 | 9/2004 | Zubok et al. |
| 2004/0176850 A1 | 9/2004 | Zubok et al. |
| 2004/0181284 A1 | 9/2004 | Simonson |
| 2004/0181285 A1 | 9/2004 | Simonson |
| 2004/0186577 A1 | 9/2004 | Ferree |
| 2004/0193272 A1 | 9/2004 | Zubok et al. |
| 2004/0220567 A1 | 11/2004 | Eisermann et al. |
| 2004/0220670 A1 | 11/2004 | Eisermann et al. |
| 2004/0243240 A1 | 12/2004 | Beaurain et al. |
| 2004/0243241 A1 | 12/2004 | Istephanous et al. |
| 2004/0249461 A1 | 12/2004 | Feree |
| 2004/0254643 A1 | 12/2004 | Jackson |
| 2005/0043800 A1 | 2/2005 | Paul et al. |
| 2005/0043802 A1 | 2/2005 | Eisermann et al. |
| 2005/0027359 A1 | 3/2005 | Mashburn |
| 2005/0071008 A1 | 3/2005 | Kirschman |
| 2005/0075644 A1 | 4/2005 | DiPoto et al. |
| 2005/0080488 A1 | 4/2005 | Schultz |
| 2005/0113916 A1 | 5/2005 | Branch, Jr. |
| 2005/0113920 A1 | 5/2005 | Foley et al. |
| 2005/0119747 A1 | 6/2005 | Fabris Monterumici et al. |
| 2005/0143820 A1 | 6/2005 | Zucherman et al. |
| 2005/0149189 A1 | 7/2005 | Mokhtar et al. |
| 2005/0149196 A1 | 7/2005 | Zucherman et al. |
| 2005/0154461 A1 | 7/2005 | Peterman et al. |
| 2005/0154462 A1 | 7/2005 | Zucherman et al. |
| 2005/0154464 A1 | 7/2005 | Eisermann et al. |
| 2005/0154465 A1 | 7/2005 | Peterman et al. |
| 2005/0154466 A1* | 7/2005 | Humphreys et al. ...... 623/17.16 |
| 2005/0154467 A1* | 7/2005 | Peterman et al. ......... 623/17.16 |
| 2005/0159818 A1 | 7/2005 | Blain |
| 2005/0165407 A1 | 7/2005 | Diaz |
| 2005/0165484 A1 | 7/2005 | Ferree |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0187625 A1 | 8/2005 | Wolek et al. |
| 2005/0192671 A1 | 9/2005 | Bao et al. |
| 2005/0197702 A1 | 9/2005 | Coppes et al. |
| 2005/0209698 A1 | 9/2005 | Gordon et al. |
| 2005/0216081 A1 | 9/2005 | Taylor |
| 2005/0234551 A1 | 10/2005 | Fallin et al. |
| 2005/0234555 A1 | 10/2005 | Sutton et al. |
| 2005/0240270 A1 | 10/2005 | Zubok et al. |
| 2005/0256578 A1 | 11/2005 | Blatt et al. |
| 2005/0261773 A1 | 11/2005 | Feree |
| 2005/0261774 A1 | 11/2005 | Trieu |
| 2005/0277930 A1* | 12/2005 | Parsons ..................... 606/61 |
| 2005/0277938 A1 | 12/2005 | Parsons |
| 2005/0283237 A1 | 12/2005 | Zucherman et al. |
| 2006/0004448 A1* | 1/2006 | Casey ..................... 623/17.11 |
| 2006/0009849 A1 | 1/2006 | Reiley |
| 2006/0036325 A1 | 2/2006 | Paul et al. |
| 2006/0069438 A1 | 3/2006 | Zucherman et al. |
| 2006/0069440 A1 | 3/2006 | Zucherman et al. |
| 2006/0085076 A1 | 4/2006 | Krishna et al. |
| 2006/0089717 A1 | 4/2006 | Krishna et al. |
| 2006/0178745 A1 | 8/2006 | Bartish, Jr. et al. |
| 2006/0241769 A1 | 10/2006 | Gordon et al. |
| 2006/0241771 A1 | 10/2006 | Gordon et al. |
| 2006/0247650 A1* | 11/2006 | Yerby et al. ................... 606/90 |
| 2007/0055378 A1 | 3/2007 | Ankney et al. |
| 2007/0179616 A1 | 8/2007 | Braddock et al. |
| 2007/0191945 A1 | 8/2007 | Yu et al. |
| 2007/0270862 A1 | 11/2007 | Yu et al. |
| 2007/0270972 A1 | 11/2007 | Gordon et al. |
| 2008/0027547 A1 | 1/2008 | Yu et al. |

FOREIGN PATENT DOCUMENTS

| | | |
|---|---|---|
| DE | 20 2004 015198 | 11/2004 |
| EP | 0 677 277 A2 | 10/1995 |
| EP | 1 281 361 A1 | 2/2003 |
| EP | 1685811 | 8/2006 |
| FR | 2 676 911 A1 | 12/1992 |
| FR | 2 799 638 | 4/2001 |
| WO | WO 96/00049 | 1/1996 |
| WO | WO 99/53871 | 10/1999 |
| WO | WO 00/04851 | 2/2000 |
| WO | WO 01/39678 | 6/2001 |
| WO | WO 01/45576 | 6/2001 |
| WO | WO 02/47586 | 6/2002 |
| WO | WO 03/041618 A2 | 5/2003 |
| WO | WO 03/045262 A2 | 6/2003 |
| WO | WO 03/084449 | 10/2003 |
| WO | WO 03/101350 | 12/2003 |
| WO | WO 2004/034935 | 4/2004 |
| WO | WO 2004/041131 | 5/2004 |
| WO | WO 2004/098465 | 11/2004 |
| WO | WO2005025431 | 3/2005 |
| WO | 2005070353 A1 | 4/2005 |
| WO | WO2005067824 | 7/2005 |
| WO | WO2005070350 | 8/2005 |

| | | |
|---|---|---|
| WO | 2005117725 A2 | 12/2005 |
| WO | WO 2005/112835 | 12/2005 |
| WO | WO2007087477 | 8/2007 |
| WO | WO2007124467 | 11/2007 |

OTHER PUBLICATIONS

U.S. Appl. No. 11/343,159, filed Jan. 30, 2006, Yu, et al.
U.S. Appl. No. 11/393,488, filed Mar. 30, 2006, Yu, et al.
U.S. Appl. No. 11/465,541, filed Aug. 18, 2006, Yu, et al.
U.S. Appl. No. 11/494,311, filed Jul. 27, 2006, Yu, et al.
Patent Cooperation Treaty—European Patent Office, "Notification of Transmittal of the International Search Report and the Written Opinion of the International Searching Authority, or the Declaration," International Application No. PCT/US2005/00586, Oct. 1, 2005, 8 pages.
Patent Cooperation Treaty—European Patent Office, "Notification of Transmittal of the International Search Report and the Written Opinion of the Internatinal Searching Authority, or the Declaration," International Application No. PCT/US2005/000648, Jun. 6, 2005, 6 pages.
Patent Cooperation Treaty—European Patent Office, "Notification of Transmittal of the International Search Report and the Written Opinion of the International Searching Authority, or the Declaration," International Application No. PCT/US2005/000705, Jun. 6, 2005, 7 pages.
Patent Cooperation Treaty—European Patent Office, "Invitation to Pay Additional Fees/Communication Relating to the Results of the Partial International Search," International Application No. PCT/US2005/000586, Jun. 8, 2005, 5 pages.
Patent Cooperation Treaty—European Patent Office, "Notification of Transmittal of the International Search Report and the Written Opinion of the Internatinal Searching Authority, or the Declaration," International Application No. PCT/US2005/000585, Jun. 8, 2005, 6 pages.
Patent Cooperation Treaty—European Patent Office, "Notification of Transmittal of the International Search Report and the Written Opinion of the Internatinal Searching Authority, or the Declaration," International Application No. PCT/US2005/000704, Aug. 23, 2005, 7 pages.
Patent Cooperation Treaty—European Patent Office, "Notification of Transmittal of the International Search Report and the Written Opinion of the International Searching Authority, or the Declaration," International Application No. PCT/US2005/000656, Aug. 23, 2005, 8 pages.
Patent Cooperation Treaty—European Patent Office, "Notification of Transmittal of the International Search Report and the Written Opinion of the International Searching Authority, or the Declaration," International Application No. PCT/US2005/000586, Dec. 16, 2005, 8 pages.
Patent Cooperation Treaty—European Patent Office, "Notification of Transmittal of the International Search Report and the Written Opinion of the International Searching Authority, or the Declaration," International Application No. PCT/US2007/060549, Dec. 2, 2007, 20 pages.
Patent Cooperation Treaty—European Patent Office, "Notification of Transmittal of the International Search Report and the Written Opinion of the International Searching Authority, or the Declaration," International Application No. PCT/US2007/074385, Dec. 19, 2007, 13 pages.
Patent Cooperation Treaty—European Patent Office, "Notification of Transmittal of the International Search Report and the Written Opinion of the International Searching Authority, or the Declaration," International Application No. PCT/US2008/065504, Mar. 3, 2009, 7 pages.
U.S. Appl. No. 11/031,602, filed Jan. 7, 2005, Humphreys et al.
U.S. Appl. No. 11/031,603, filed Jan. 7, 2005, Humphreys et al.
U.S. Appl. No. 11/031,700, filed Jan. 7, 2005, Humphreys et al.
U.S. Appl. No. 11/031,780, filed Jan. 7, 2005, Hodges et al.
U.S. Appl. No. 11/031,781, filed Jan. 7, 2005, Peterman et al.
U.S. Appl. No. 11/031,783, filed Jan. 7, 2005, Humphreys et al.
U.S. Appl. No. 11/031,903, filed Jan. 7, 2005, Humphreys et al.
U.S. Appl. No. 11/031,904, filed Jan. 7, 2005, Peterman et al.

* cited by examiner

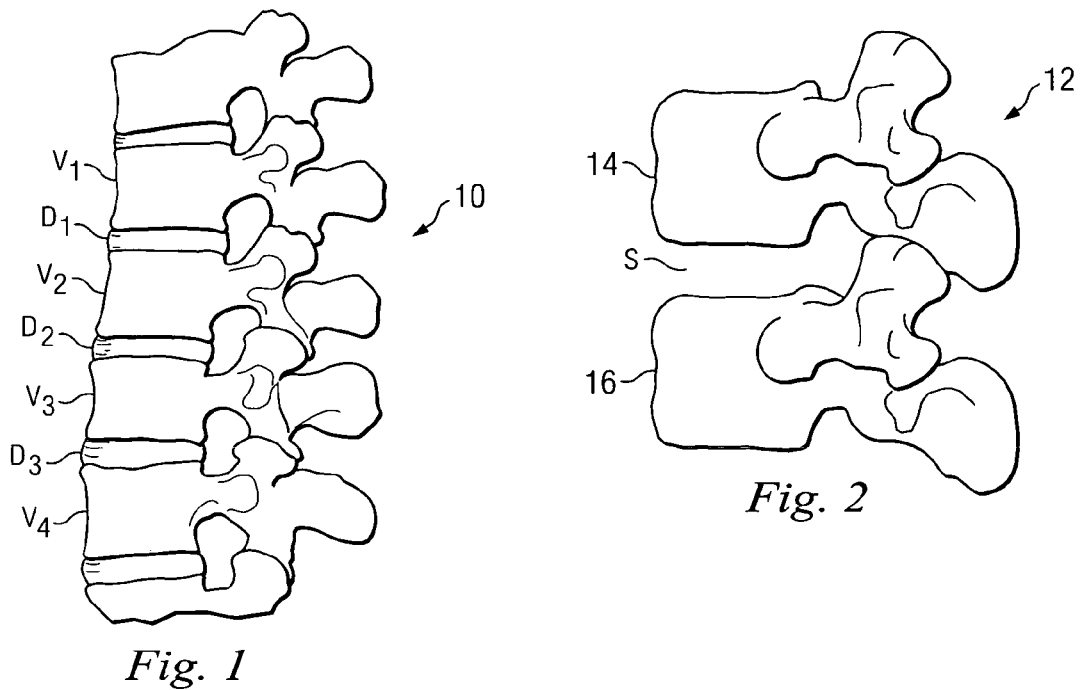
Fig. 1
Fig. 2
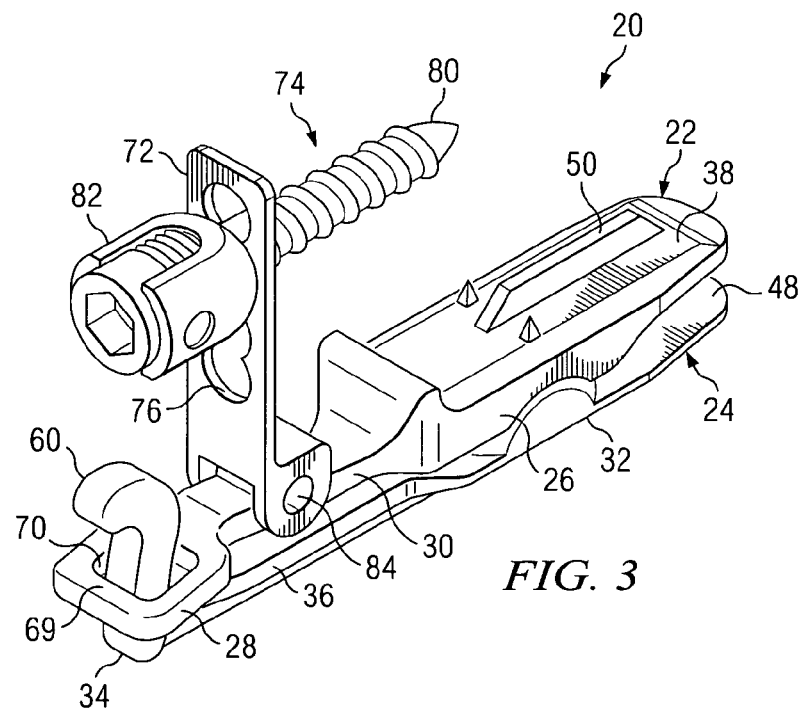
FIG. 3

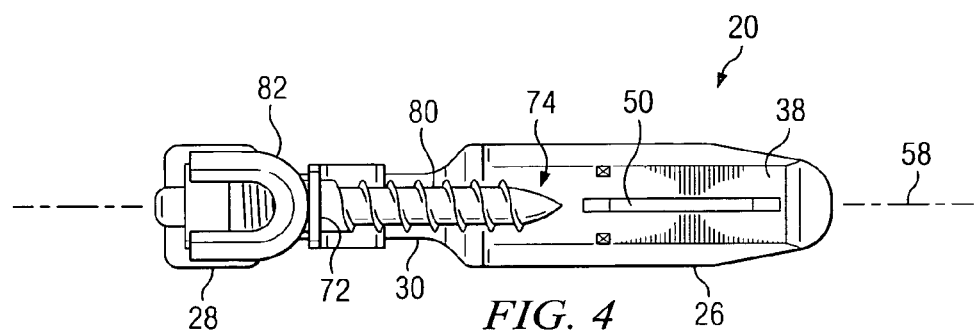
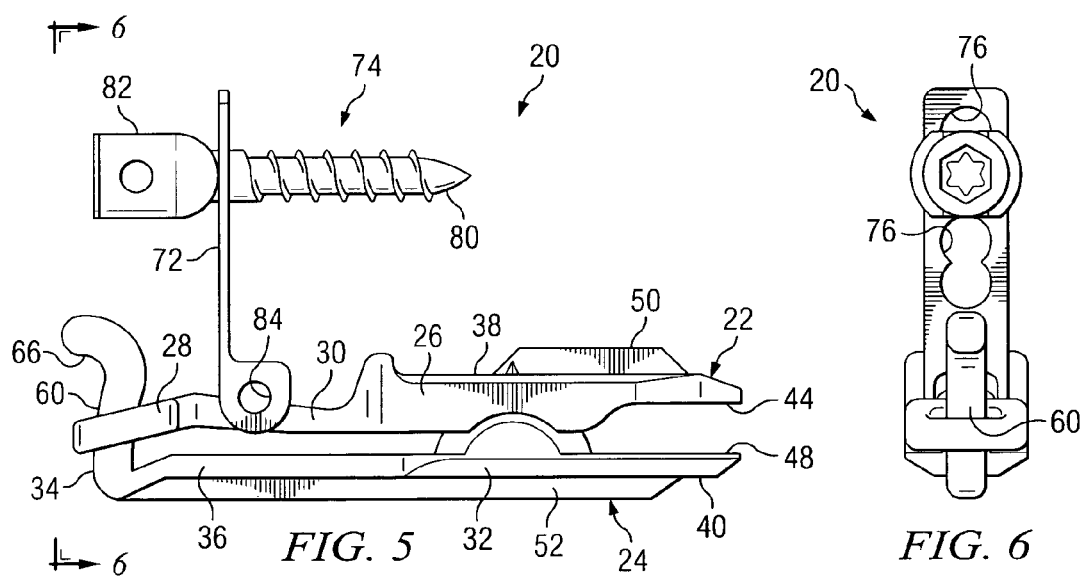

POSTERIOR JOINT REPLACEMENT DEVICE

BACKGROUND

Disc arthroplasty is one way of treating injured, degraded, or diseased spinal joints. Some disc arthroplasty treatments include replacing injured discs of the joint with a motion-preserving spinal disc that allows some articulation or movement of the spinal joint. Often, these motion-preserving spinal discs are attached to the adjacent vertebra using screws as fasteners. Sometimes, the location of the screws can be less than ideal, potentially resulting in some weakening of the vertebra and potentially not sufficiently securing the motion-preserving spinal discs in place. Such a less-than-ideal attachment can limit the operability of the motion-preserving spinal disc.

What is needed is a prosthetic device for insertion into an intervertebral space that may be better secured to the vertebral column or that may more effectively provide desired characteristics. The posterior joint replacement device disclosed herein overcomes one or more problems in the prior art.

SUMMARY OF THE INVENTION

In one exemplary aspect, the present disclosure is directed to a prosthetic device for placement in an intervertebral space defined between an upper vertebra and a lower vertebra to provide articulating motion to the upper and lower vertebrae. The prosthetic device may include an upper articular portion configured to be at least partially disposed in the intervertebral space and a lower articular portion configured to be at least partially disposed in the intervertebral space. The lower articular portion may be configured to cooperate with the upper articular portion to provide articulating motion to the upper and lower vertebrae.

In another aspect, an attachment element may extend from one of the upper and lower articular portions in the general direction of the spinal column. The attachment element may be configured to be fastened to at least one of the upper and the lower vertebrae to at least partially secure in place said one of the upper and lower articular portions.

In yet another exemplary aspect, this disclosure is directed to a motion-preserving prosthetic device component for placement in an intervertebral space defined between an upper vertebra and a lower vertebra. The prosthetic device may include an articular portion configured to be at least partially disposed in the intervertebral space. The articular portion may be configured to cooperate with a mating portion to provide articulating motion to the upper and lower vertebrae. The articular portion may include a body and an attachment element.

In another aspect, the body may be configured to be fixed relative to one of the upper and lower vertebrae. The attachment element may be configured to be fastened to said one of the upper and lower vertebrae at a location outside of and spaced from the intervertebral space.

In another aspect, the attachment element may be flexible. The body may be configured to be fixed relative to one of the upper and lower vertebrae, and the flexible attachment element may be configured to attach to the other of the upper and lower vertebrae.

In another exemplary aspect, this disclosure is directed to a prosthetic device for placement in an intervertebral space defined between an upper vertebra and a lower vertebra. The device may include the motion-preserving prosthetic device component as a first articular portion. A second articular portion may be configured to cooperate with the first articular portion to provide articulating motion to the upper and lower vertebrae. The second articular portion may be configured to be fixed relative to the other of the upper and lower vertebrae.

In yet another exemplary aspect, this disclosure is directed to a method of implanting a prosthetic device in an intervertebral space defined between an upper vertebra and a lower vertebra to provide articulating motion to the upper and lower vertebrae. The method may include placing an upper articular portion at least partially in the intervertebral space and placing a lower articular portion at least partially in the intervertebral space. The lower articular portion may cooperate with the upper articular portion to provide articulating motion to the upper and lower vertebrae. An attachment element extending from one of the upper and lower articular portions in the general direction of the spinal column may be fastened to at least one of the upper and the lower vertebrae outside the intervertebral space to at least partially secure in place said one of the upper and lower articular portions.

In some exemplary aspects, the joint replacement device disclosed herein may include one or more features disclosed in the following prior patent applications, incorporated herein in their entirety by reference:

U.S. Utility patent application Ser. No. 11/031,602, filed on Jan. 7, 2005 and entitled "Spinal Arthroplasty Device and Method;"

U.S. Utility patent application Ser. No. 11/031,603, filed on Jan. 7, 2005 and entitled "Dual Articulating Spinal Device and Method;"

U.S. Utility patent application Ser. No. 11/031,780, filed on Jan. 7, 2005 and entitled "Split Spinal Device and Method;"

U.S. Utility patent application Ser. No. 11/031,904, filed on Jan. 7, 2005 and entitled "Interconnected Spinal Device and Method;"

U.S. Utility patent application Ser. No. 11/031,700, filed on Jan. 7, 2005 and entitled "Support Structure Device and Method;"

U.S. Utility patent application Ser. No. 11/031,783, filed on Jan. 7, 2005 and entitled "Mobile Bearing Spinal Device and Method;"

U.S. Utility patent application Ser. No. 11/031,781, filed on Jan. 7, 2005 and entitled "Centrally Articulating Spinal Device and Method;" and U.S. Utility patent application Ser. No. 11/031,903, filed on Jan. 7, 2005 and entitled "Posterior Spinal Device and Method."

BRIEF DESCRIPTION OF THE DRAWINGS

FIG. 1 is a pictorial representation of a lateral view of a portion of a vertebral column.

FIG. 2 is a pictorial representation of a lateral view of a pair of adjacent vertebral bodies defining an intervertebral space.

FIG. 3 is a pictorial representation of an isometric view of an exemplary intervertebral prosthetic device.

FIG. 4 is a pictorial representation of a top view of an exemplary intervertebral prosthetic device.

FIG. 5 is a pictorial representation of a side view of an exemplary intervertebral prosthetic device.

FIG. 6 is a pictorial representation of an end view of an exemplary intervertebral prosthetic device.

DETAILED DESCRIPTION

Figure 7:
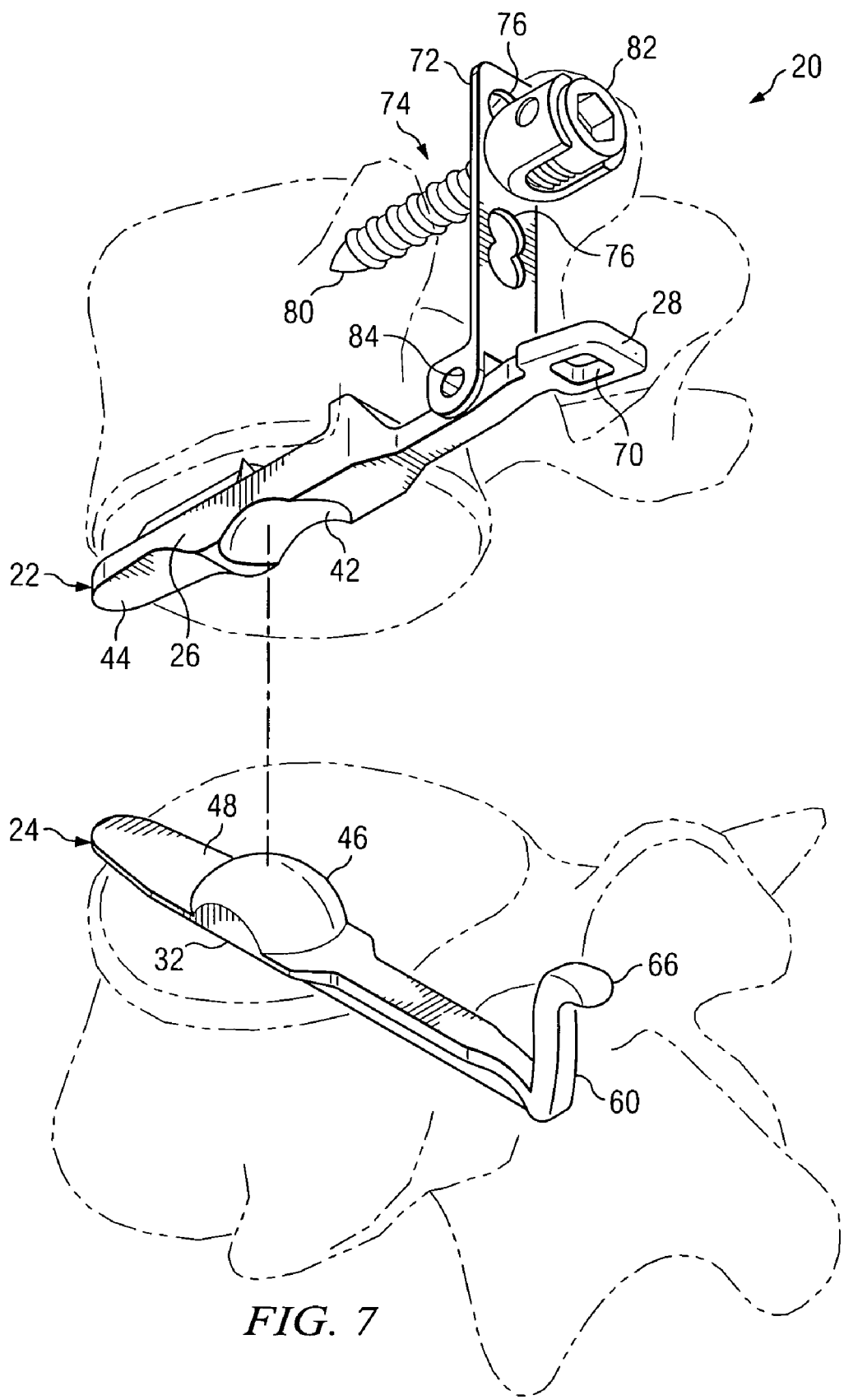
FIG. 7 is a pictorial representation showing inner features of an intervertebral prosthetic device.

The present invention relates generally to vertebral reconstructive devices and, more particularly, to an intervertebral prosthetic device for implantation. For the purposes of promoting an understanding of the principles of the invention, reference will now be made to embodiments or examples illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a lateral view of a portion of a spinal column 10, illustrating a group of adjacent upper and lower vertebrae V1, V2, V3, V4 separated by natural intervertebral discs D1, D2, D3. The illustration of four vertebrae is only intended as an example. Another example would be a sacrum and one vertebrae.

For the sake of further example, two of the vertebrae will be discussed with reference to FIG. 2. The two vertebrae form a spinal segment 12 including an upper vertebra 14 and a lower vertebra 16. Some types of disc arthroplasty require that some or all of the natural disc that would have been positioned between the two vertebrae 14, 16 be removed via a discectomy or a similar surgical procedure. Removal of the diseased or degenerated disc results in the formation of an intervertebral space S between the upper and lower vertebrae 14, 16. Although the illustration of FIG. 2 generally depicts the spinal segment 12 as a lumbar vertebral joint, it is understood that the devices, systems, and methods of this disclosure may also be applied to all regions of the vertebral column, including the cervical and thoracic regions. It should be understood that in this description and in the claims of this disclosure, the terms upper and lower vertebrae also contemplate vertebra that do not directly form the intervertebral space S, but that are at locations respectively above and below those vertebra that directly form the intervertebral space S.

Some conventional spinal prosthetic devices are installed using an anterior procedure, requiring a physician to access the spinal column using distressing and sometimes traumatic procedures. Once a prosthetic is installed using an anterior procedure, scar tissue may build on sensitive vessels. If a second procedure is required, a physician may be required to remove the scar tissue to access the previously placed prosthetic. This sensitive procedure can cause additional distress to the patient. The intervertebral prosthetic device disclosed herein may be advantageous over prior devices because it may be installed using a posterior procedure. Accordingly, a physician need not access and disturb the critical vessels that reside at the anterior side of the spinal column. Further, if a second procedure becomes necessary, the physician has easy access to the previously placed prosthetic without removing scar tissue off of sensitive vessels. Accordingly, the procedure may be simplified and may cause less distress to the patient.

Some implantation procedures require placement of fasteners that secure the prosthetic device in place. In conventional systems, these fasteners are typically driven into the vertebral body. However, the vertebral bodies in some patients, including many older patients, can become weak, and may become less than desirable locations for anchoring. Because of this, over time, the fasteners in the vertebral body may become loose and begin to toggle, risking displacement of the implanted prosthetic disc. The fasteners also may present additional problems. For example, fasteners are typically driven into the side of the vertebral body, just above or below the vertebral space. Accordingly, the fasteners might lie shallowly in the vertebra, in close proximity to the endplate. This shallow location may potentially slow the bone growth rate at the endplates, as the bone mates with the surface of the prosthetic device. In addition, the shallow location of the fastener may weaken the endplate of the vertebra, and if subjected to extreme loads, the vertebra may split, potentially requiring additional surgeries and replacement prosthetic devices. The intervertebral prosthetic devices disclosed herein may allow the device fasteners to be introduced to the vertebra at a location spaced away from the vertebral endplate, and in some instances, into the pedicles rather than the vertebral bodies.

Figure 8A:
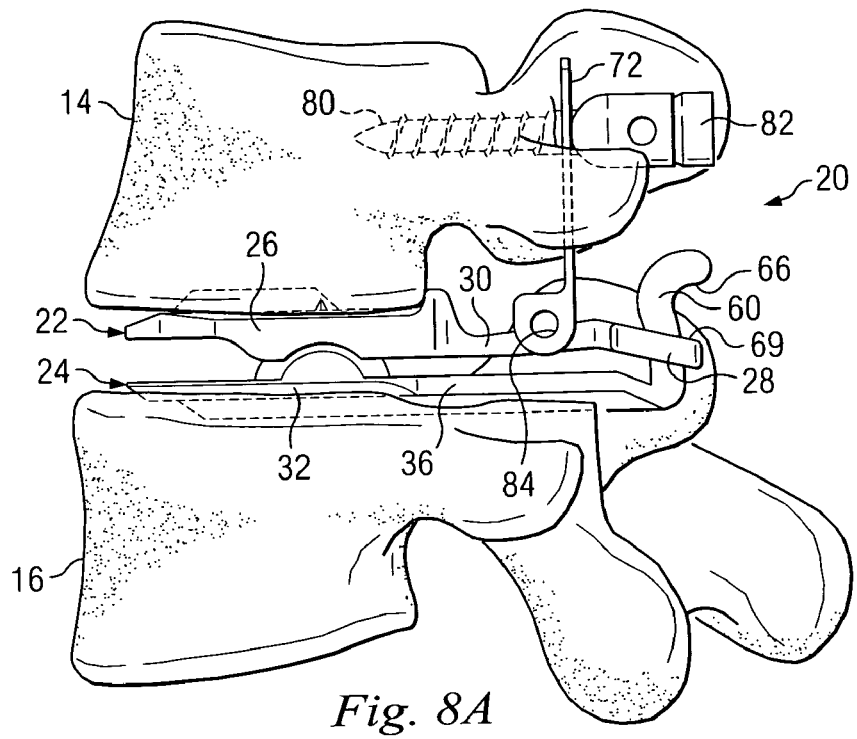
FIGS. 8A and 8B are pictorial representations of an intervertebral prosthetic device in an intervertebral space.
Figure 8B:
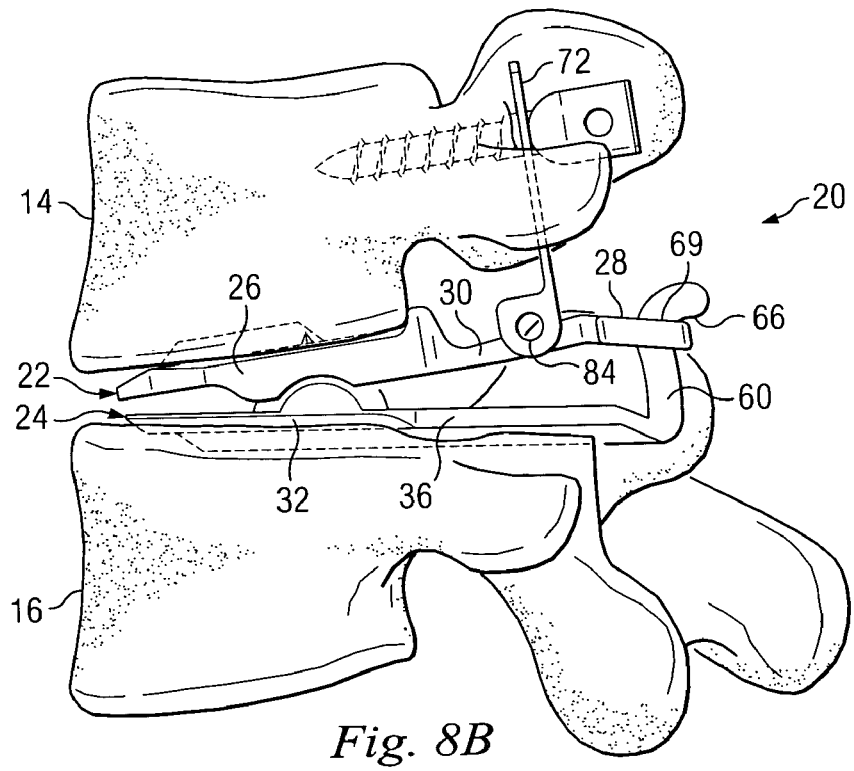

FIGS. 3-7 show a number of views of a prosthetic device 20 implantable in the intervertebral space S of FIG. 2. FIGS. 8A and 8B show the prosthetic device 20 in place in the intervertebral space S. The prosthetic device 20 allows the vertebra 14 to articulate relative to the vertebra 16 to provide movement to the spinal joint. Sized to fit the intervertebral space height in a manner similar to a natural intervertebral disc, such as any of discs D1-D4, the prosthetic device 20 provides support and stabilization to the vertebrae FIG. 3 is an isometric view of the prosthetic device 20, and FIG. 4 is a top view. FIG. 5 is a side view and FIG. 6 is an end view. FIG. 7 shows portions of the prosthetic device 20 separate to display inner features. With reference to FIG. 3-7, the prosthetic device 20 includes an upper articular portion 22 and a lower articular portion 24. The upper articular portion 22 includes an upper main body formed of an interdiscal section 26, a posterior section 28, and a bridge 30 extending between the interdiscal and posterior sections 26, 28. Similarly, the lower articular portion 24 includes a lower main body formed of an interdiscal section 32, a posterior section 34, and a bridge 36 extending between the interdiscal and posterior sections 32, 34.

The upper and lower articular portions 22, 24 may be formed of any suitable biocompatible material including metals such as cobalt-chromium alloys, titanium alloys, nickel titanium alloys, and/or stainless steel alloys. Ceramic materials such as aluminum oxide or alumina, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various sections comprising the upper articular portion 22 and the lower articular portion 24 may be formed of different materials thus permitting metal on metal, metal on ceramic, metal on polymer, ceramic on ceramic, ceramic on polymer, or polymer on polymer constructions.

In the exemplary embodiment shown, each of the upper and lower articular portions 22, 24 are integrally formed or molded of a single piece of material. In other embodiments, one or more of the interdiscal, posterior, and bridge sections of either of the upper or lower articular portions 22, 24 may be formed separately and attached to one or more of the other sections. Attachments in these embodiments may be accomplished using any fastening mechanism known in the art including, for example, a threaded connection, a bolted connection, or a latched connection, among others. In those embodiments, the interdiscal, posterior, and bridge sections also may be formed of different materials.

The interdiscal section 26 of the upper articular portion 22 may include a bone contacting surface 38 and an inner surface 44 opposite the bone contacting surface 38. A first articular surface 42 may form a part of the inner surface 44 (FIG. 7). In the embodiment shown, the first articular surface 42 is a recess. Similarly, the interdiscal section 32 of the lower articular portion 24 may include a bone contacting surface 40 opposite an inner surface 48, with a second articular surface 46 forming a part of the inner surface 48 (FIG. 7) and being configured to mate with the first articular surface 42. In the embodiment shown, the second articular surface 46 is a protrusion.

Together, the first and second articular surfaces 42, 46 may form an articulating joint that allows the upper and lower articular portions 22, 24 to articulate relative to each other. This articulation, in turn, may allow articulating movement of the upper vertebra 14 relative to the lower vertebra 16, and in some embodiments, may allow movement similar to that provided by a natural spinal disc. In the embodiment shown, the second articular surface 46 is a partial sphere that may rotate or translate within the first articular surface 42, forming a loosely constrained ball and socket style joint. Although shown as a ball and socket joint, the first and second articular surfaces 42, 46 may be any shape or design that allows one of the upper and lower articular portions 22, 24 to move relative to the other of the upper and lower articular portions 22, 24. For example, the first and second articular surfaces 42, 46 may include a trough and recess, a ball and saucer, or other shaped features. In some embodiments, the first and second articular surfaces 42, 46 are formed of a material different than the remainder of the interdiscal sections 26, 32 to provide suitable articulation.

The bone contacting surfaces 38, 40 of the upper and lower articular portions 22, 24 may include features or coatings which enhance the fixation of the implanted prosthetic device 20. For example, the surfaces 38, 40 may be roughened such as by chemical etching, bead-blasting, sanding, grinding, serrating, and/or diamond-cutting. All or a portion of the bone contacting surfaces 38, 40 of the upper and lower articular portions 22, 24 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures and features.

In the exemplary embodiment shown, optional upper and lower bone connectors 50, 52 are formed on the bone contacting surfaces 38, 40, respectively. These bone connectors 50, 52 extend toward the upper and lower vertebrae 14, 16 in a manner to help secure the upper and lower articular portions 22, 24 in place. In the example shown, the bone connectors 50, 52 are keels configured to extend into notches or grooves formed into the vertebral endplates. The bone connectors also could be a series of ridges, protrusions, or other surface features that help fix the prosthetic device 20 in place.

The bridge sections 30, 36 extend rearward from the interdiscal sections 26, 32 respectively. In the embodiment shown, the bridge sections 30, 36 extend substantially along a longitudinal centerline 58 (FIG. 4) of the prosthetic device 20. In other embodiments, the bridge sections do not align with a longitudinal centerline of the interdiscal sections, but may be curved or angled to depart away from the longitudinal centerline.

The posterior sections 28, 34 may be disposed at the end of the bridge sections 30, 36 and, in some embodiments, may be configured to fit adjacent to the processes of the vertebrae 14, 16. The posterior section 34 of the lower articular portion 24 may include a tail 60 extending generally in a direction along the spinal column, and past the posterior section 28 of the upper articular portion 22.

The tail 60 may connect to the bridge section 36 and, in the example shown, is formed by a bend in the bridge section 36. Extending upwardly, the tail 60 may be at least partially disposed at a location higher than the bridge section 36. Part of the tail 60 may form a motion stop 66 (FIG. 5) configured to limit the range of articulation between the upper and lower articular portions 22, 24. In the embodiment shown, the motion stop 66 is a bend in the tail 60 having a length that is configured to work together with the upper articular portion 22 to limit the available range of articular rotation of the upper and lower articular portions 22, 24. It should be noted that the tail 60 may be substantially straight or may be curved, angled or otherwise formed. In one exemplary embodiment, the tail 60 may include a curve concentric with the curvature of the protruding articular surface 46.

The posterior section 28 of the upper articular portion 22 includes an aperture 70 formed therein that is configured to receive the tail 60 of the lower articular portion 24. In the embodiment shown, a portion of the posterior section 28 forms a motion stop 69 that is configured to cooperate with the motion stop 66 on the tail 60. Accordingly, when the upper and lower articular portions 22, 24 are assembled as shown in FIG. 5, the motion stop 66 and the motion stop 69 cooperate to limit the range of articulation of the prosthetic device 20. In addition, the aperture 70 is configured so that when the articulating surfaces 42, 46 are mated, the tail 60 extends through the aperture 70 in a manner that articulation may still freely occur within the range.

Because of the configuration of the motion stops 66, 69, the upper and lower articular portions 22, 24 may be configured for assembly when outside of the intervertebral space S of FIG. 2. Further, the upper and lower articular portions 22, 24 may be difficult to disassemble within the intervertebral space S. Therefore, the chance of the upper and lower articular portions 22, 24 becoming misaligned after implantation is reduced. Furthermore, the tail 60 and aperture 70 reduce the chance of axial rotation of one of the upper and lower articular portions 22, 24 about the other of the upper and lower articular portions 22, 24. Accordingly, despite forming a ball and socket joint, the upper and lower articular portions 22, 24 are bound together so that axial rotation is limited by the aperture 70 and the tail 60.

In the embodiment shown, the upper articular portion includes an attachment element, such as a plate 72, extending upwardly from the upper main body of the upper articular portion 22 and a fastener 74. The plate 72 is configured to connect the fastener 74 to the upper main body, and is configured to lie along the pedicle of the adjacent vertebra so that the fastener 74 extends into the pedicle (FIGS. 8A and 8B). In the embodiment shown, the plate 72 has a width greater than the width of the bridge 30 and extends from the bridge. An aperture 76 allows passage of the fastener 74 through the plate 72 into the adjacent vertebra. The aperture 76 includes a scalloped profile 78 that, in the example shown, is formed by overlapping holes, with each hole allowing passage of the fastener 74. In the example shown, the scalloped profile 78 is formed of two separate sections showing two holes each, providing four placement options for the fastener. Accordingly, a physician implanting the prosthetic device 20 may choose which of the available options to insert the fastener 74. It should be noted that in other embodiments, a different number of apertures or holes may be used.

The fastener 74 may be a bone screw having a threaded portion 80 for insertion into bone and a head 82 operable to press against the plate 72 to secure the plate against the bone. The fastener 74 may be inserted into the bone substantially in a plane formed through the longitudinal axis, and in the embodiment shown, the fastener 74 is substantially parallel to the longitudinal axis. In the embodiment shown the head itself has a diameter greater than the diameter of the holes of the scalloped profile 78 of the plate 72 and is in contact with the plate. Washers or other hardware may be used with the fastener 74 to secure the plate to the bone. One exemplary fastener suitable for use with the plate 72 is described further below with reference to FIG. 10. Although shown as a screw, the fastener 74 may be any other fastener that can secure the plate in place.

A joint 84 may allow the plate 72 to move relative to the upper main body of the upper articular portion 22. In the example shown, the joint 84 is a hinge providing movement of the plate 72 relative to the upper main body along the direction of the longitudinal centerline 58. Providing a degree of freedom to the plate 72 may allow simpler placement of the plate 72 against the pedicle and may compensate for any space between the plate and the pedicle. In some embodiments, securing the plate 72 in place to the pedicle and securely locating the interdiscal section 26 of the upper articular portion 22 to the endplate of the vertebra 14, effectively locks the joint 84 in place.

The plate 72 and joint 84 allow the prosthetic device 20 to be fastened to the pedicle, rather than the vertebral body by providing an attachment location spaced away from the intervertebral space S. Accordingly, the prosthetic device 20 is connected to the stronger bones in the vertebral column, that provide additional support. This may reduce the chance of the fastener coming loose or toggling over time. This also reduces problems that might arise when the fastener is disposed very close to the vertebral endplates. This may find particular utility in patients whose vertebral bodies may have began to grow relatively brittle.

FIGS. 8A and 8B are side views of the prosthetic device 20 between upper and lower vertebrae 14, 16. As shown, the interdiscal section 26 may be situated along an inferior surface of the upper vertebra 14 and the interdiscal section 32 may be situated above a superior surface of the lower vertebra 16. However, it should be understood by one of ordinary skill in the art that the two interdiscal sections 26, 32 are not limited to such an arrangement, and may be oriented in different positions and/or shaped differently than what is illustrated herein.

FIG. 8A shows the device 20 when the spinal column is in a natural position, while FIG. 8B shows the device 20 when the spinal column is in flexion. Although not shown, the prosthetic device 20 also allows articulation in extension. Referring to FIG. 8B, when in flexion, the motion stop 69 on the posterior section 28 of the upper articular portion 22 is in contact with the motion stop 66 of the lower articular portion 24. Accordingly, a flexion/extension and/or torsional articulation range of the prosthetic device 20 is limited to the amount allowed by the motion stops 66 and 69. FIG. 8A shows the prosthetic device 20 articulated to a substantially central position, with the aperture 70 being disposed about the middle region of the tail 60. When in extension, in some embodiments, the articulation range is limited by the bridge sections 30, 36, which can act as motion stops to limit the articulation between the upper and lower articular portions 22, 24. In the example shown, the total range of motion of the prosthetic device 20 may be about 45 degrees. However, the range of motion could be more or less than this, as controlled by the motion stops.

Figure 9:
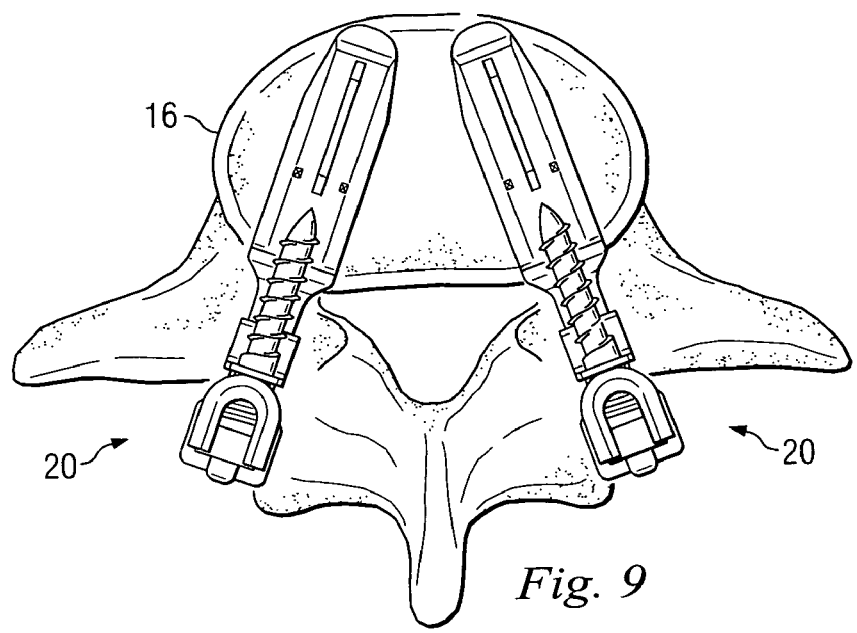
FIG. 9 is a pictorial representation of intervertebral prosthetic devices disposed on a lower vertebra.

FIG. 9 shows a top view of the prosthetic device 20 in place on the lower vertebra 16. As apparent in FIG. 9, the prosthetic device 20 may be configured for placement on one half of an interdiscal space, while a second prosthetic device 20 may be placed on the other half of the interdiscal space. Accordingly, in some embodiments, a complete prosthetic disc may include a pair of prosthetic devices 20, one for the left and the other for the right, that cooperate together to take the place of the natural disc. It should be readily apparent that the right and left prosthetic devices 20 may be substantially similar in structure and function.

Figure 10:
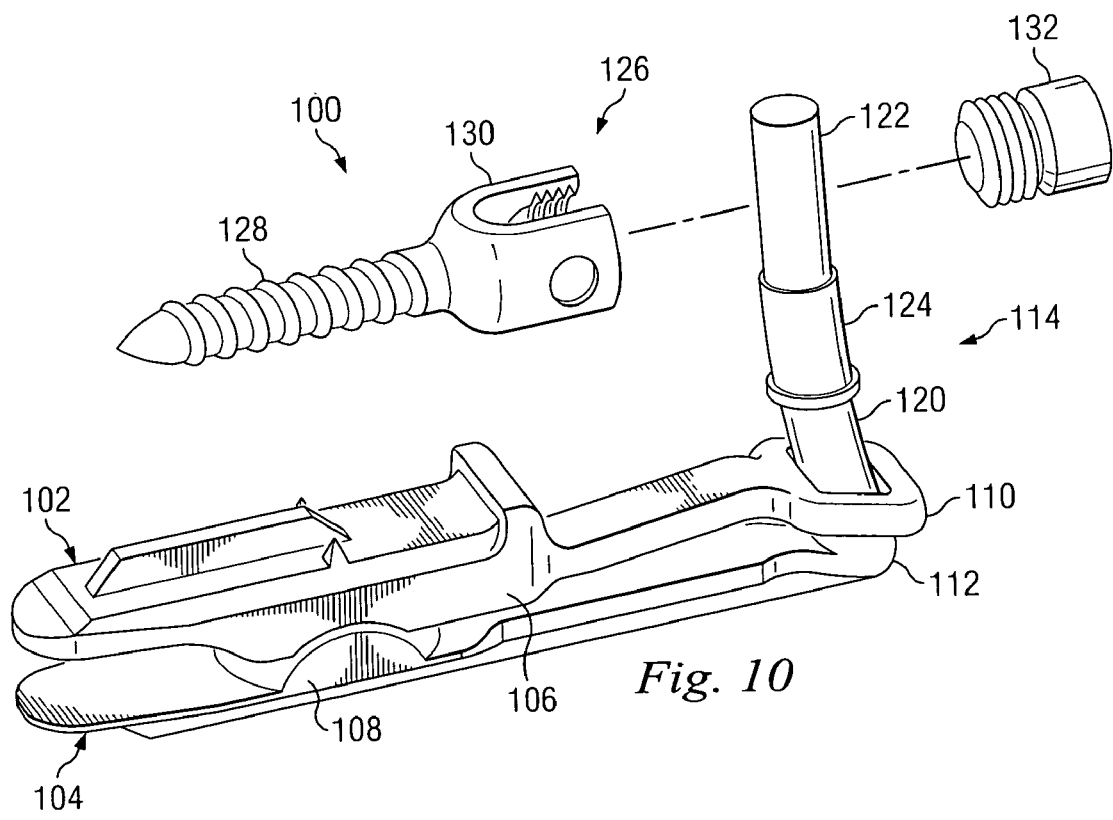
FIG. 10 is a pictorial representation of an isometric view of an exemplary intervertebral prosthetic device according to another aspect of this disclosure with an exploded fastener.
Figure 11:
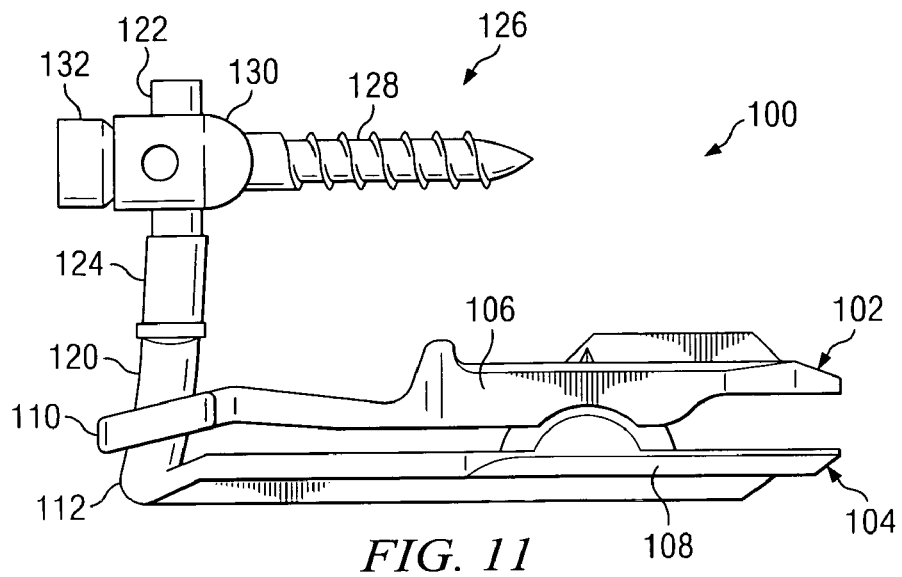
FIG. 11 is a pictorial representation of a side view of an exemplary intervertebral prosthetic device.
Figure 12:
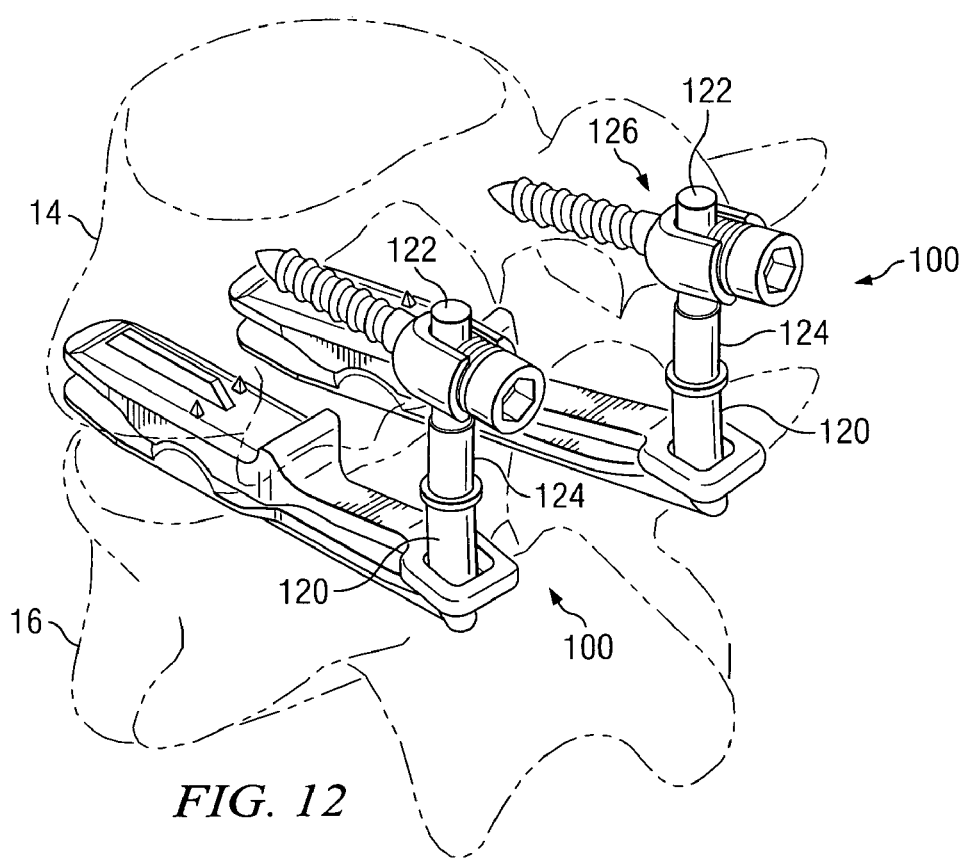
FIG. 12 is a pictorial representation of an exemplary intervertebral prosthetic device within an intervertebral disc space.

Another embodiment of an articular prosthetic device 100 is shown in FIGS. 10-12. The articular prosthetic device 100 has many features similar to the articular prosthetic device 20 described above. A detailed description of these features will not be repeated here. However, it is understood that any feature described above with respect to the device 20 may be applied to the device 100 and vice-versa.

The articular prosthetic device 100 includes an upper articular portion 102 and a lower articular portion 104, each having an interdiscal section 106, 108 and each having a posterior section 110, 112, respectively. Instead of a connecting plate 72 as described above, the prosthetic device 100 includes an attachment element, such as a tail 114, extending from the lower articular portion 104, through the aperture in the upper articular portion 102, to connect to the upper vertebra 14. Therefore, in this embodiment, the lower articular portion 104 connects to the upper vertebra 14.

A healthy vertebral column distributes carried loads so that about 80% of the load is carried in the anterior regions of the vertebrae and about 20% of the load is carried in the facets. Upon removal of the facets through a posterior surgical procedure, the anterior regions of the vertebrae typically carries a full 100% of the load. In the embodiment in FIGS. 10-12, the tail 114 connects the upper vertebra 14 to the lower articular portion 104 so that a percentage of any applied loads are carried not solely by the anterior portions of the vertebra, but also by the posterior portion. Accordingly, by distributing applied loads between both the anterior portion and the posterior portion, the prosthetic device 100 has a load distribution that more closely matches the natural vertebral column than does conventional prosthetic devices.

Furthermore, because posterior implantation procedures often include removal of facet joints or processes that operate as connection locations for ligaments and muscles, their removal may limit the ability of the joint to control the range of joint articulation. Accordingly, conventional prosthetic devices implanted through a posterior procedure provide articulation, but it may be largely uncontrolled. With the removal of the muscles and ligaments, the repaired joint may become floppy. The intervertebral prosthetic device disclosed herein may dampen the articulation, thereby providing more stability and more control to the spinal column.

The tail 114 includes a lower tail portion 120, an upper tail portion 122, and a flexible bumper 124. The lower tail portion 120 may be formed similar to the tail 60 described above, and may be an integral part of the lower articular portion 104 or alternatively, may be connected to the lower articular portion 104 through a connector such as, for example, a joint, a bracket, or other system. The upper tail portion 122 is suitable for attachment to a fastener 126. In the example shown, the upper tail portion 122 is a straight rod. However, the upper tail portion 122 may be straight or curved to provide leverage and desired load distribution to the lower articular portion 104. The upper and lower tail portions 122, 120 may be formed of any material suitable for the prosthetic device 100. In some embodiments, the upper and lower tail portions 122, 120 are formed of the same material, while in others, they are formed of different materials.

The flexible bumper 124 may allow for relative movement between the upper and lower tail portions 122, 120. This mobility enables the upper and lower vertebrae 14, 16 to move in flexion and extension despite the lower articular portion 104 being connected to both the upper and lower vertebrae 14, 16. The flexible bumper 124 may be formed of any suitable biocompatible material including, for example, elastomeric materials and polymers, among other materials. In the example shown, the flexible bumper 124 is in-line with the upper and lower tail portions 122, 120. However, in other embodiments, the flexible bumper 124 may have a diameter or thickness greater than or less than the diameter or thickness of the upper and lower tail portions 122, 120. In some examples, the flexible bumper 124 is over-molded onto the upper and lower tail portions 122, 120. In other examples, the upper and lower tail portions 122, 120 may be secured through a metal cable extending from the upper to the lower tail portion, with an elastomeric cushion provided to transfer loads at the posterior of the vertebral column. In one embodiment, the cable may be secured at each end, for example, within the upper and lower tail portions 122, 120, and may limit the range of extension, while the flexible bumper 124 may control the amount of flexion. In other embodiments, the cable is not secured to limit the range of flexion or extension, and instead simply secures the various tail portions together.

As shown in FIG. 10, the fastener 126 may be configured to adjustably connect to the vertebra 14 and the upper tail portion 122. Here, the fastener 126 includes a bone section 128 and a head section 130. The bone section 128 may include threads and may configured to connect to the bone in a manner known in the art. In this exemplary embodiment, the head section 130 is formed with a U-shape configured to receive the upper tail portion 122. A set-screw 132 may be driven into the U-shape, securing the upper tail portion 122 in place between the set-screw 132 and the base of the U-shape. In the example shown, the set-screw 132 includes outer threads that mate with inner threads in the U-shape. Loosening the set screw 132 releases the tail 114, which can then by adjusted or manipulated to a desired position. Tightening the set screw 132 then secures the tail 114 in place.

The fastener 126 may be driven into the vertebra in a direction substantially parallel to a longitudinal axis 134 of the prosthetic device 100. In one example, the fastener 126 is driven into the pedicles, while in another embodiment, the fastener is driven into the vertebral body.

The prosthetic devices 20, 100 may be implanted between the vertebrae 14, 16 as will be described below. Generally, as discussed above, the artificial intervertebral prosthetic devices 20, 100 may be implanted into a body using a posterior transforaminal approach similar to the known transforaminal lumbar interbody fusion (TLIF) or posterior lumbar interbody fusion (PLIF) procedures. PLIF approaches are generally more medial and rely on more retraction of the traversing root and dura to access the vertebral interspace. TLIF approaches are typically more oblique, requiring less retraction of the exiting root, and less epidural bleeding with less retraction of the traversing structures. It is also possible to access the interspace using a far lateral approach. In some instances it is possible to access the interspace via the far lateral without resecting the facets. Furthermore, a direct lateral approach through the psoas is known. This approach avoids the posterior neural elements completely. It is anticipated that embodiments of the prosthetic devices 20, 100 could utilize any of these common approaches.

According to at least one of these approaches, an incision, such as a midline incision, may be made in the patient's back and some or all of the affected disc and surrounding tissue may be removed via the foramina. The superior endplate surface of the vertebra 14 may be milled, rasped, or otherwise resected to match the profile of the bone contacting surface of the upper articular portion to normalize stress distributions on the superior endplate surface of the vertebra 14 and/or to provide initial fixation prior to bone ingrowth. The preparation of the endplate of vertebra 14 may result in a flattened surface or in surface contours such as pockets, grooves, or other contours that may match corresponding features on the bone contacting surface 38. The inferior endplate of the vertebra 16 may be similarly prepared to receive the lower articular portion to the extent allowed by the exiting nerve root and the dorsal root ganglia. In some procedures, the natural facet joints of vertebrae 14, 16 may be trimmed or removed to make room for the posterior sections of the articular portions.

The upper and lower articular portions of the prosthetic device may then be oriented so that the tail extends through the aperture. The upper and lower articular portions then may be simultaneously introduced into the transforaminal openings and are placed in the appropriate intervertebral disc space between the upper and lower vertebrae. In some procedures, the upper and lower articular portions may be introduced through a cannula. If the pieces are modular, the prosthetic device may be implanted pieces at a time, with posterior sections of the upper and lower articular portions introduced last.

The bridge sections may extend in a posterior direction from the interdiscal sections and in a posterior direction from the intervertebral intervertebral space S. The posterior sections are positioned in a posterior direction of the intervertebral disc space to replace or supplement the function of the natural facet joints.

Referring to the prosthetic device 20, the plate 72 may be rotated about its joint 84 so that it is in contact with the bone. The physician may select an appropriate hole in the aperture 76 with its scalloped profile 78 for introducing the fastener 74. The selection may be based upon the location that the physician believes is most ideal for securing the fastener 74 into the bone. A hole may be drilled into the bone through the aperture, and the fastener 74 may be driven into the hole. It should be noted that in some embodiments the plate is not in direct contact with the bone, but spacers, washers, or bumpers may be disposed between the plate and the bone.

Referring to the prosthetic device 100, the physician may select an appropriate location to place the fastener 126, preferably at a location that permits the flexible bumper 124 on the tail 114 to be disposed between the fastener 126 and the intervertebral space S. A hole may be drilled into the bone and the fastener 126 may be driven into the hole. The tail 114 then may be secured to the fastener 126 outside the discal space S.

As installed, the ball and socket type joint created by the articular surfaces 42, 46 may be relatively stable and self-centering. Both the anterior joint and the posterior connection (formed by the tail and aperture connection) allow the prosthetic device 20 to resist shear forces, particularly anterior-posterior forces. Further, rotational motion about a longitudinal centerline defined by the cylindrical bodies 14, 16 may be limited both by the constraint in the tail and aperture connection and by the combined constraint provided by utilizing two prosthetic devices.

The robust and forgiving structure of the anterior joint and the tail and aperture connection permits misalignment and slight inaccuracy in the placement of the prosthetic devices. For example, the ball and socket structure of the articular joint tolerates a certain amount of misalignment between the components. The interaction of the tail and aperture may also accommodate parallel misalignment and/or anterior-posterior misalignment between the prosthetic devices 20, 21. In some embodiments, a single unilateral prosthetic device may be implanted, while in others, two devices, forming a right and a left device may be implanted.

In some embodiments, the tail 114 is formed of a single rigid piece and a flexible bumper. For example, the tail may include a lower tail portion that extends from the articular portion. The flexible bumper then may extend from the lower portion and be secured in the fastener. Accordingly, in such an embodiment, an upper tail portion may be eliminated from the design. In yet another embodiment, the tail portion is formed entirely of the flexible bumper, so that the entire tail is flexible. Other embodiments, including multiple flexible portions and multiple rigid portions are also contemplated.

In some embodiments, both the upper and lower articular portions include tails having at least a flexible portion. In these embodiments, the tails extend past each other so that the tail from the lower articular portion extends to connect to the upper vertebra and the tail from the upper articular portion extends to connect to the lower vertebra. These tails may be formed to have similar or different levels of flexibility to provide desired dampening and load distribution. The upper and lower articular portions may or may not include apertures for receiving the opposing tails.

Similarly, in some embodiments, both the upper and lower articular portions include plates. These plates may extend from the main bodies of the articular portions and allow each articular portion to be secured to the respective vertebra. Each plate may have one or more apertures, that may be scalloped, that provide more than a single location for a fastener. It should be noted than in any embodiment, the plate may be connected to the main body of the articular portion at locations other than the bridge section. For example, in some embodiments, the plate extends from the posterior section.

In some embodiments, the prosthetic device includes both plates and a tail having a flexible bumper. In some of these embodiments, the plate and the tail may use the same fastening screw or separate fastening screws.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. In the claims, means-plus-function clauses are intended to cover the elements described herein as performing the recited function and not only structural equivalents, but also equivalent elements.

We claim:

1. A prosthetic device for placement in an intervertebral disc space defined between an upper vertebra and a lower vertebra to provide articulating motion to the upper and lower vertebrae, comprising:

an upper articular portion configured to be at least partially disposed in the intervertebral disc space, the upper articular portion including an upper posterior portion configured to be disposed at a location posterior of the intervertebral disc space;

a lower articular portion configured to be at least partially disposed in the intervertebral disc space and configured to cooperate with the upper articular portion to provide articulating motion to the upper and lower vertebrae, the lower articular portion including a lower posterior portion configured to be disposed at a location posterior of the intervertebral disc space; and an attachment element extending from the upper posterior portion and when implanted extends in the general direction of the spinal column, the attachment element being configured to be fastened to the upper vertebra to at least partially secure in place the upper articular portion, wherein the upper and lower articular portions are laterally symmetric about an anterior-posterior longitudinal centerline and the attachment element is centrally aligned about the longitudinal centerline, wherein the attachment element is connected to the upper posterior portions by a movable joint centrally aligned about the longitudinal centerline, and wherein the upper and lower posterior portions extend in a substantially parallel direction when the prosthetic device is in a neutral position.

2. The prosthetic device of claim 1, including a fastener configured to fasten the attachment element to at least one of the upper and lower vertebrae.

3. The prosthetic device of claim 2, wherein the fastener adjustably connects to the attachment element.

4. The prosthetic device of claim 2, wherein the fastener is configured to align substantially along the centerline of said one of the upper and lower articular portions.

5. The prosthetic device of claim 2, wherein the fastener includes a bone anchor screw.

6. The prosthetic device of claim 1, wherein the attachment element is configured to receive a fastener at a plurality of selectable locations.

7. The prosthetic device of claim 1, wherein the joint provides a degree of freedom to the attachment element.

8. The prosthetic device of claim 1, wherein the attachment element includes at least one aperture configured to receive a fastener.

9. The prosthetic device of claim 1, wherein the attachment element extends at least to pedicle of the upper or lower vertebrae.

10. A method of implanting a prosthetic device in an intervertebral disc space defined between an upper vertebra and a lower vertebra to provide articulating motion to the upper and lower vertebrae, comprising:

placing an upper articular portion at least partially in the intervertebral disc space, the upper articular portion having an upper posterior portion configured to be disposed at a location posterior of the intervertebral disc space;

placing a lower articular portion at least partially in the intervertebral disc space, the lower articular portion having a lower posterior portion configured to be disposed at a location posterior of the intervertebral disc space, wherein the lower articular portion cooperates with the upper articular portion to provide articulating motion to the upper and lower vertebrae, the lower posterior portion connected by a joint to an attachment element;

aligning the upper and lower articular portions about a longitudinal centerline such that the upper and lower articular portions are symmetric about the longitudinal centerline and such that the upper and lower posterior portions are substantially parallel when the prosthetic device is in a neutral position;

centrally aligning the joint about the longitudinal centerline;

positioning the joint posteriorly of vertebral bodies of the upper and lower vertebrae; and fastening the attachment element extending from the lower posterior portion in the general direction of the spinal column to the upper vertebra outside the intervertebral disc space to at least partially secure in place said one of the upper and lower articular portions.

11. The method of claim 10, wherein fastening the attachment element includes attaching the attachment element to a head of a fastener.

12. The method of claim 10, wherein fastening the attachment element includes connecting the attachment element to the upper vertebra to provide flexible dampening to the articulating motion.

13. The method of claim 10, wherein placing the upper articular portion and placing the lower articular portion are performed simultaneously.

* * * * *